United States Patent
Roessl

(10) Patent No.: US 10,470,721 B2
(45) Date of Patent: Nov. 12, 2019

(54) DETECTOR AND IMAGING SYSTEM FOR X-RAY PHASE CONTRAST TOMO-SYNTHESIS IMAGING

(71) Applicant: KONINKLIJKE PHILIPS N.V., Eindhoven (NL)

(72) Inventor: Ewald Roessl, Ellerau (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 203 days.

(21) Appl. No.: 15/528,992

(22) PCT Filed: Nov. 17, 2015

(86) PCT No.: PCT/EP2015/076734
§ 371 (c)(1),
(2) Date: May 23, 2017

(87) PCT Pub. No.: WO2016/083182
PCT Pub. Date: Jun. 2, 2016

(65) Prior Publication Data
US 2017/0303867 A1  Oct. 26, 2017

(30) Foreign Application Priority Data
Nov. 24, 2014 (EP) ..................................... 14194482

(51) Int. Cl.
*A61B 6/00* (2006.01)
*A61B 6/02* (2006.01)
*A61B 6/04* (2006.01)

(52) U.S. Cl.
CPC ............ *A61B 6/025* (2013.01); *A61B 6/0414* (2013.01); *A61B 6/4035* (2013.01);
(Continued)

(58) Field of Classification Search
None
See application file for complete search history.

(56) References Cited

U.S. PATENT DOCUMENTS 8,073,099 B2  12/2011  Niu
9,068,919 B2   6/2015  Handa
(Continued)

FOREIGN PATENT DOCUMENTS

WO  2011070493 A1  6/2011
WO  2013004574 A1  1/2013
(Continued)

OTHER PUBLICATIONS

Arboleda, Carolina et al "Tilted-Grating Approach for Scanning-Mode X_Ray Phase Contrast Imaging", Optics Express, vol. 22, No. 13, P15447, 2014.
(Continued)

*Primary Examiner* — Hoon K Song
(74) *Attorney, Agent, or Firm* — Larry Liberchuk

(57) ABSTRACT

The invention relates to an X-ray detector arrangement (10) for X-ray phase contrast tomo-synthesis imaging, a line detector (1) for X-ray phase contrast tomo-synthesis imaging, an imaging system (24) for X-ray phase contrast tomo-synthesis imaging, a method for X-ray phase contrast tomo-synthesis imaging, and a computer program element for controlling such arrangement and a computer readable medium having stored such computer program element. The X-ray detector arrangement (10) comprises several line detectors (1). Each line detector (1) is configured to detect a Moiré pattern in at least a portion of an X-ray beam (2) impacting such line detector (1). Each line detector (1) comprises several detector lines (11), wherein a width W of each line detector (1) equals one period or an integer multiple of the period of the Moiré pattern.

13 Claims, 4 Drawing Sheets

(52) U.S. Cl.
CPC .......... *A61B 6/4233* (2013.01); *A61B 6/4291* (2013.01); *A61B 6/484* (2013.01); *A61B 6/502* (2013.01)

(56) References Cited

U.S. PATENT DOCUMENTS

| | | | |
|---|---|---|---|
| 2009/0110144 | A1 | 4/2009 | Takahashi |
| 2012/0153181 | A1 | 6/2012 | Iwakiri |
| 2012/0163537 | A1 | 6/2012 | Iwakiri |
| 2012/0307966 | A1 | 12/2012 | Roessl |
| 2015/0055743 | A1* | 2/2015 | Vedantham ............ G01N 23/04 378/36 |
| 2016/0252470 | A1* | 9/2016 | Momose .......... G01N 23/20075 378/36 |

FOREIGN PATENT DOCUMENTS

| | | |
|---|---|---|
| WO | 2013111050 A1 | 8/2013 |
| WO | 2013126296 A1 | 8/2013 |

OTHER PUBLICATIONS

Roessl, E. et al "Clinical boundary conditions for grating-based differential phase contrast mammography" Philosophical Transactions of the Royal Society, 2014, 372, 20130033.

Momose, A. et al "High-speed X-ray phase imaging and X-ray phase tomography with Talbot interferometer and white synchrotron radiation," Opt. Express 17(15), 12540-12545 (2009).

Li, Ke et al "Grating-based Phase Contrast Tomosynthesis Imaging: Proof-of-Concept Experimental Studies", Medical Physics, vol. 41, 2014.

Szafraniec, Magdalena et al Proof-of-Concept Demonstration of Edge-Illumination X-Ray Phase Contrast Imaging Combined with Tomosynthesis, Physics in Medicine and Biology, vol. 59, 2014.

Momose, A. et al "High-Speed X-Ray Phase Imaging with Grating Interferometer and White Synchrotron Light", The 10th International Conf. on Synchrotron Radiation Instrumentation, 2010.

* cited by examiner

DETECTOR AND IMAGING SYSTEM FOR X-RAY PHASE CONTRAST TOMO-SYNTHESIS IMAGING

CROSS-REFERENCE TO PRIOR APPLICATIONS

This application is the U.S. National Phase application under 35 U.S.C. § 371 of International Application No. PCT/EP2015/076734, filed on Nov. 17, 2015, which claims the benefit of European Patent Application No. 14194482.7, filed on Nov. 24, 2014. These applications are hereby incorporated by reference herein.

FIELD OF THE INVENTION

The invention relates to an X-ray detector arrangement for X-ray phase contrast tomo-synthesis imaging, a line detector for X-ray phase contrast tomo-synthesis imaging, an imaging system for X-ray phase contrast tomo-synthesis imaging, a method for X-ray phase contrast tomo-synthesis imaging, and a computer program element for controlling such arrangement and a computer readable medium having stored such computer program element.

BACKGROUND OF THE INVENTION

In X-ray image acquisition technology, an object to be examined is situated between an X-ray source and an X-ray detector. A fan- or cone-beam is generated by the X-ray source, possibly employing collimation elements, in the direction of the X-ray detector. The object to be examined is spatially attenuating the X-ray beam depending on its inner structure. The spatially attenuated X-radiation is subsequently arriving at the X-ray detector, with the intensity distribution of the X-radiation being determined and subsequently converted to electrical signals for further processing and display of an X-ray image. Both the X-ray generating device and the X-ray detector may be mounted on a gantry for rotation around the object to be examined. By providing an according rotation with subsequent acquisition of different X-ray images of varying alignment and orientation with respect to the object to be examined, a three-dimensional reconstruction of the objects inner morphology may be obtained.

In addition to such X-ray transmission imaging, a phase-contrast imaging may determine a phase-shift of the transmitted X-rays and a scattering power of a sample. This provides additional information that may be employed for contrast enhancement, determining material composition and reducing X-radiation dosage. WO 2013/004574 (A1) thereto discloses an X-ray imaging system for phase-contrast imaging comprising an X-ray source, a phase grating, an analyzer grating and an X-ray detector element. An object to be imagined is arrangeable between the X-ray source and the X-ray detector element. The phase grating as well as the analyzer grating is arrangeable between the X-ray source and the X-ray detector element. The X-ray source, the phase grating, the analyzer grating and the X-ray detector are operatively coupled for acquisition of a phase-contrast image of the object.

Carolina Arboleda et al, "Tilted-grating approach for scanning mode X-ray phase contrast imaging", Optics express, vol. 22, no. 13, page 15447, discloses employing titled gratings for a scanning phase contrast imaging system.

WO 2013/126296 discloses a scanning phase contrast imaging system.

SUMMARY OF THE INVENTION

There may be a need to provide an X-ray detector arrangement for phase-contrast imaging, which combines the acquisition of tomosynthesis data with the acquisition of phase contrast data in a simple manner.

The problem of the present invention is solved by the subject-matters of the independent claims, wherein further embodiments are incorporated in the dependent claims. It should be noted that the aspects of the invention described in the following apply also to the X-ray detector arrangement for X-ray phase contrast tomo-synthesis imaging, the line detector for X-ray phase contrast tomo-synthesis imaging, the imaging system for X-ray phase contrast tomo-synthesis imaging, the method for X-ray phase contrast tomo-synthesis imaging, the computer program element, and the computer readable medium.

According to the present invention, an X-ray detector arrangement for X-ray phase contrast tomo-synthesis imaging is presented. The X-ray detector arrangement comprises several line detectors. Each line detector is configured to detect a Moiré pattern in at least a portion of an X-ray beam impacting such line detector. Each line detector comprises several detector lines, wherein a width of each line detector equals one period or an integer multiple of the period of the Moiré pattern. In this manner, a simultaneous acquisition of phase contrast data is facilitated by an equidistant phase sampling on adjacent detector lines of one (or an integer multiple) of the Moiré fringe period.

The invention thereby proposes an X-ray detector arrangement capable to combine the acquisition of tomosynthesis data with the acquisition of phase contrast data. As explained above, X-ray phase contrast imaging is a method that uses information concerning changes in the phase of an X-ray beam that passes through an object in order to create its images. The X-ray beam's phase shift caused by a sample is not measured directly, but is transformed into variations in intensity, which then can be recorded by the detector. X-ray tomo-synthesis is a method for performing high-resolution limited-angle tomography at e.g. mammographic dose levels. Tomography refers to imaging by sections or sectioning, through the use of any kind of penetrating wave. The invention applies to an X-ray detector arrangement for e.g. X-ray tomo-synthesis and slit-scanning phase-contrast mammography and in particular Full-Field-Digital mammography.

The combination of phase-contrast imaging and tomo-synthesis is achieved in a simple manner, as it requires only a minimal extension of the line detector geometry. The extension of the geometry of a "conventional" slit scanning tomo-synthesis system to a phase-contrast slit scanning tomo-synthesis system is simple and minimal, because the X-ray detector and collimator structure remain in place. The necessary hardware change amounts to replacing the e.g. 21 conventional line detectors with the same number of line detectors according to the invention, wherein each of the line detectors features several (e.g. eight) adjacent detector lines. Further, the Moiré pattern period is adjusted to the total lateral coverage of the line detector width (e.g. eight sensor channels to sample at least one complete period of intensity modulation due to phase-contrast effects.

Exemplarily, each line detector comprises at least three detector lines. Three detector lines are minimal to determine the three parameters related to the attenuation, the phase shift and the scattering power of a sample. Exemplarily, each line detector comprises between four and sixteen detector lines. More than sixteen detector lines do not improve the accuracy of the phase determination any further in case the fringe period equals the detector width. In an example, each detector line is segmented into eight segments which appears a very practical number for segmentation in terms of a compromise between complexity and accuracy. Each line detector may comprise a sensor with an anode and a cathode. For segmenting a line detector into several detector lines, its anode may be segmented into several anode strips.

In an example, each detector line is arranged along a direction perpendicular to the axis of symmetry of the X-ray beam. The axis of symmetry of the X-ray beam is used as reference system as the X-ray beam can be e.g. cone shaped and thereby divergent along its width, which means that sub-beams of the X-ray beam are slightly inclined (and not parallel) to each other. Nevertheless, all detector lines are aligned in the same plane, which means they are parallel and not inclined relative to each other.

In another example, each detector line is inclined in a non-perpendicular direction relative to the axis of symmetry of the X-ray beam. The inclination improves an X-ray stopping power of the detector lines. Exemplarily, each detector line may be inclined with an acute angle relative to the axis of symmetry of the X-ray beam. The acute angle may be between 5° and 40°. Also in this example, all detector lines are still parallel to each other.

In an example, several grating components configured to create a Moiré pattern in the X-ray beam are provided such that one grating component is arranged in front of each line detector when seen in the direction of the X-ray beam. The advantage of the grating component as several sub-units is a higher flexibility e.g. when adjusting the Moiré pattern period equally over the entire detector In another example, one grating unit configured to create a Moiré pattern in the X-ray beam is provided such that the grating unit is arranged in front of and covers all line detectors at the same time when seen in the direction of the X-ray beam. The advantage of the grating unit as single unit is a higher simplicity and robustness in the system.

In an example, the grating component or the grating unit configured to create a Moiré pattern comprises a source grating, a phase grating and an analyzer grating. The Moiré pattern is used for a retrieval of the differential phase. In detail, the Moiré pattern may be created as a superposition of a self-image of the phase grating and a pattern of the analyzer grating, wherein both gratings have related periodicity and are inclining to each other by a very small angle. This Moiré pattern may act as carrier fringes and thus the phase gradient introduced by the object can be detected as a displacement of the Moiré pattern. With a Fourier analysis of the Moiré pattern, a phase-contrast image of the object can be extracted together with information about the scattering power of the object.

According to the present invention, also a line detector for X-ray phase contrast tomo-synthesis imaging is presented. The line detector is configured to detect at least a Moiré pattern in a portion of an X-ray beam impacting such line detector and comprises several detector lines. A width of the line detector equals one period or an integer multiple of the period of the Moiré pattern. In an example, the Moiré pattern in the X-ray beam is created by a grating component or grating units. The grating component or each grating unit comprises a source grating, a phase grating and an analyzer grating, where the source grating may be common to all the phase-gratings and analyzer gratings.

According to the present invention, also an imaging system for X-ray phase contrast tomo-synthesis imaging of an object is presented. The imaging system comprises an X-ray detector arrangement as described above, an X-ray source arrangement and a gantry. The X-ray source arrangement, the grating arrangement and the X-ray detector arrangement are mounted to the gantry.

In an example, the imaging system further comprises an object support configured to support the object, wherein the imaging system is configured for relatively moving the object support and the gantry. In an example, the imaging system is configured for rotating the gantry and/or the object support, around an axis of rotation situated below the X-ray detector arrangement when seen in the direction of the X-ray beam, such that a relative movement between the gantry and the object support is realized. By providing such rotation with subsequent acquisition of different X-ray images of varying alignment and orientation with respect to the object to be examined, a three-dimensional reconstruction of the objects inner morphology may be obtained. In an example, the imaging system is configured for translating, optionally in addition to aforementioned rotating, the gantry and/or the object support in a direction perpendicular to the axis of symmetry of the X-ray beam, again in order to effectuate a relative movement between the gantry and the object support.

The system may comprise a grating component or a set of grating units mounted to the gantry. A line detector of the X-ray detector arrangement may be adapted such that each of its detector lines is segmented into several, e.g. at least 4 segments. The detector lines may be orientated either in a direction perpendicular to the axis of symmetry of the X-ray beam or may be inclined in a non-perpendicular direction to the axis of symmetry of the X-ray beam to sample the interference pattern i.e. to reconstruct phase. In both cases, all detector lines are aligned in the same plane, which means they are parallel and not inclined relative to each other.

According to the present invention, also a method for X-ray phase contrast tomo-synthesis imaging is presented. It comprises the following steps:
a) providing an X-beam passing through an X-ray detector arrangement, and
b) detecting a Moiré pattern in at least a portion of the X-ray beam.

The X-ray detector arrangement comprises several line detectors, wherein each line detector is configured to detect the Moiré pattern in at least a portion of the X-ray beam. Each line detector comprises several detector lines and a width of each line detector equals one period or an integer multiple of the period of the Moiré pattern.

In an example, the method comprises the further step of c) using data detected by the detector lines of each line detector for generating an attenuation image, a phase-contrast image and a scatter image of the object being examined based on phase detection or iterative reconstruction.

Depending in the physical width of the line-detectors in relation to the system's spatial resolution in the same direction, step c) above can either be performed under the assumption that the attenuation, the phase-gradient and the scattering are constant over the width of a detector line or not. In the first case, the phase-retrieval process is identical to phase-retrieval from phase-stepping data. In the second case, iterative techniques need to be employed to obtain images of the attenuation, the phase shift and the scattering power of the sample.

According to the present invention, also a computer program element is presented, wherein the computer program element comprises program code means for causing an X-ray detector arrangement for X-ray phase contrast tomo-synthesis imaging as defined in the independent device claim to carry out the steps of the method for X-ray phase contrast tomo-synthesis imaging when the computer program is run on a computer controlling the X-ray detector arrangement.

It shall be understood that the X-ray detector arrangement for X-ray phase contrast tomo-synthesis imaging, the line detector for X-ray phase contrast tomo-synthesis imaging, the imaging system for X-ray phase contrast tomo-synthesis imaging, the method for X-ray phase contrast tomo-synthesis imaging, the computer program element for controlling such devices and the computer readable medium having stored such computer program element according to the independent claims have similar and/or identical preferred embodiments, in particular, as defined in the dependent claims. It shall be understood further that a preferred embodiment of the invention can also be any combination of the dependent claims with the respective independent claim.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the accompanying drawings.

DETAILED DESCRIPTION OF EMBODIMENTS

Exemplarily, grating-based, differential phase contrast mammography is described in the following. Implementations of such differential phase contrast mammography make use of the inherent redundancy of data acquisition in slit-scanning mammography. To simultaneously acquire attenuation-, phase- and dark-field information for a two-dimensional image of a (female) breast, it is necessary to measure the X-ray intensity down-stream a Talbot-Lau interferometer (comprising a source grating, a phase grating and an analyzer grating and relying on coherent self-imaging of periodic gratings) for e.g. eight different relative lateral displacements between the local phase-, and analyzer gratings pitch for one and the same geometrical ray. This can be achieved by a process named phase-stepping but not necessarily in this way. In case of attenuation imaging by mammographic slit scanning, each geometric ray is sampled e.g. 18 times by 18 different detector pixels. This redundancy is only used for reducing noise but does not lead to new signals in the attenuation case. In differential-phase contrast slit-scanning mammography, the acquisition from 18 different detector lines does provide information equivalent to phase-stepping, with the advantage of the absence of the need for the actuation of highly aligned, micron-sized structures.

In implementations of tomo-synthesis systems based on slit-scanning, the geometrical redundancy on the geometrical ray basis is lost because the rotational scan is no longer performed around the X-ray focal spot but around a point below the slit scanning detector unit. The rotational scan comprises a relative rotation between (i) an aggregate of X-ray detector, gratings and X-ray source and (ii) the object to be examined. The data so acquired can be used to reconstruct 3D voxel data sets of the mammographic density of the female breast with all know complications of limited-angle tomography.

It is therefore clear that a straightforward generalization of phase-contrast mammography to phase-contrast tomo-syntheses is all but obvious for slit-scanning geometries. According to this invention, the combination of phase-contrast imaging and tomo-synthesis is achieved by an elegant, simple and minimal extension of the line detector geometry.

The extension of the geometry of a slit scanning tomo-synthesis system to a phase-contrast slit scanning tomo-synthesis imaging system according to the invention is called elegant, simple and minimal, because the X-ray detector and its collimator structure can remain in place. The necessary hardware change amounts to replacing the e.g. 18 conventional line detectors with the same number of line detectors according to the invention, wherein each of the line detectors now features of the order of e.g. eight adjacent detector lines. A pitch of the adjacent detector lines can either be identical to the conventional width of the line detector or smaller.

Figure 1:
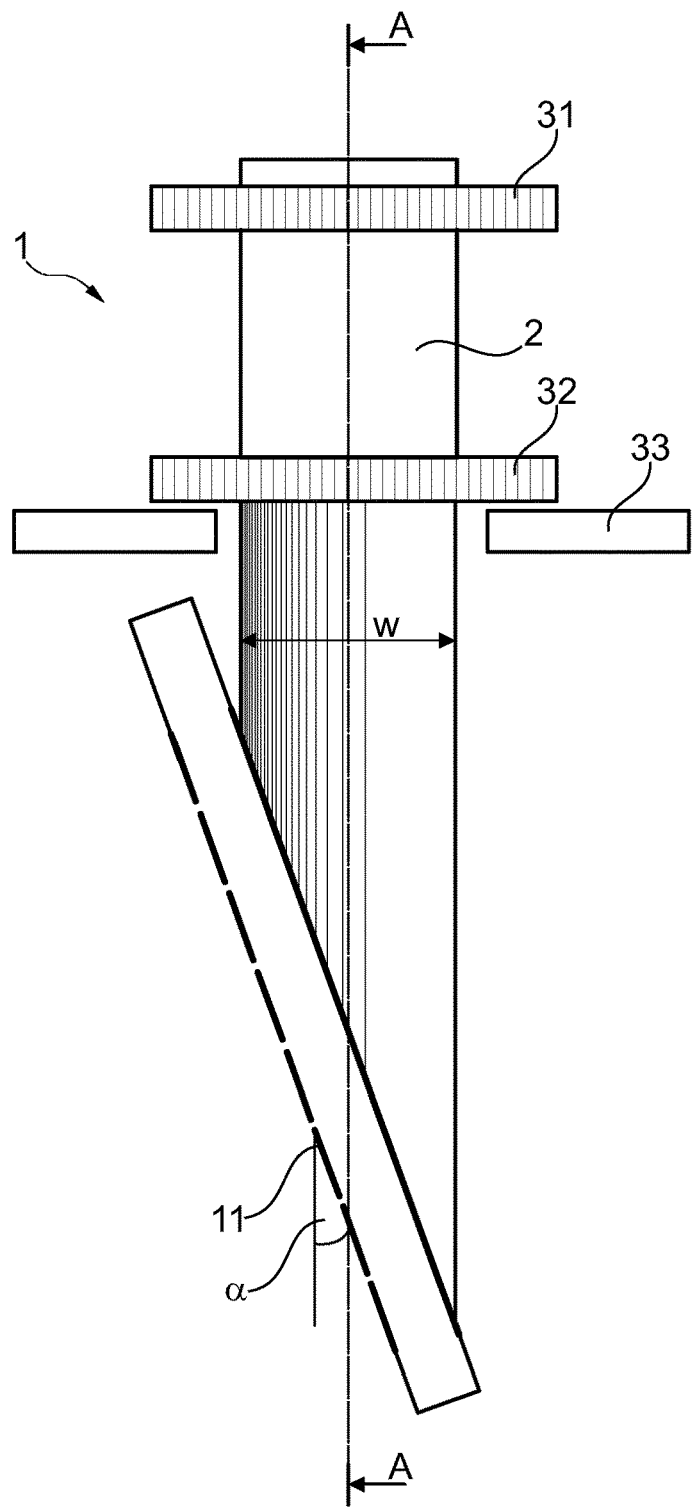
FIG. 1 shows a schematic drawing of a line detector for X-ray phase contrast tomo-synthesis imaging according to the invention.

FIG. 1 shows schematically and exemplarily a detail of an X-ray detector arrangement 10 for X-ray phase contrast tomo-synthesis imaging according to the invention. The X-ray detector arrangement 10 comprises several line detectors 1. In FIG. 1, only one line detector 1 for X-ray phase contrast tomo-synthesis imaging according to the invention is shown. A multiplicity of such line detectors 1 arranged adjacent to each other gives X-ray detector arrangement 10 for X-ray phase contrast tomo-synthesis imaging according to the invention (see FIG. 2). Each of these line detectors 1 is configured to detect a Moiré pattern in at least a portion of an X-ray beam 2 impacting such line detector 1. Each line detector 1 comprises several detector lines 11, wherein a width W of each line detector 1 equals one period or an integer multiple of the period of the Moiré pattern. FIG. 1 thereto shows one line detector 1 with eight detector lines 11.

In FIG. 1, X-ray beams 2 are incident from the top of the figure indicated by the shaded band passing a Talbot-Lau interferometer comprising a phase-grating 31 and an analyzer grating 32. After the passage of the analyzer grating 32, a Moiré pattern is formed in the downstream intensity between two post-collimator blades 33 indicative of the changes induced by the presence of an object (upstream, not shown in the Figure) in terms of attenuation, phase-shift and scattering. In a conventional system, a single detector line 11 in form of a Si-sensor with a single Si-strip anode is used. In contrast thereto, the line detector 1 according to the invention and as shown in FIG. 1 comprises eight independent detector lines 11 in form of eight independent anode strips, or in other words, eight pixels of a pixelated silicon anode structure to sense the Moiré pattern.

The Moiré pattern frequency is adjusted to the total coverage of the (in the shown implementation) eight anode strips or sensor channels to sample at least one complete period of intensity modulation due to phase-contrast effects.

The Moiré pattern formed after the interferometer will be sensed by here eight independent readout channels allowing phase-retrieval with the Fourier method for each frame of readout. The channel density is thereby increased by a factor of eight.

In FIG. 1, the detector lines 11 are inclined in a non-perpendicular direction with an acute angle α relative to the axis A of symmetry of the X-ray beam 2. The detector lines 11 are inclined to improve an X-ray stopping power of the detector lines 11. In other words, a grazing-angle illumination of Si-wafers as detector lines 11 is used to improve stopping power in contrast to conventional systems. For example, the X-ray beam 2 after two post-collimator blades 33 has a width of about 100 micrometer. Due to the strongly inclined incidence on the detector lines 11, the X-ray beam 2 widens to a millimeter-sized footprint on the sensor surface. This effect renders the channel density on the detector lines 11 in the plane of the drawing comparable to the channel density perpendicular to the drawing (e.g. a chest-wall-mammilla direction). The shown inclination of the detector lines 11 is optional. Also a non-inclined 2D detector is possible e.g. in case a sensor with higher atomic number is used.

Figure 2:
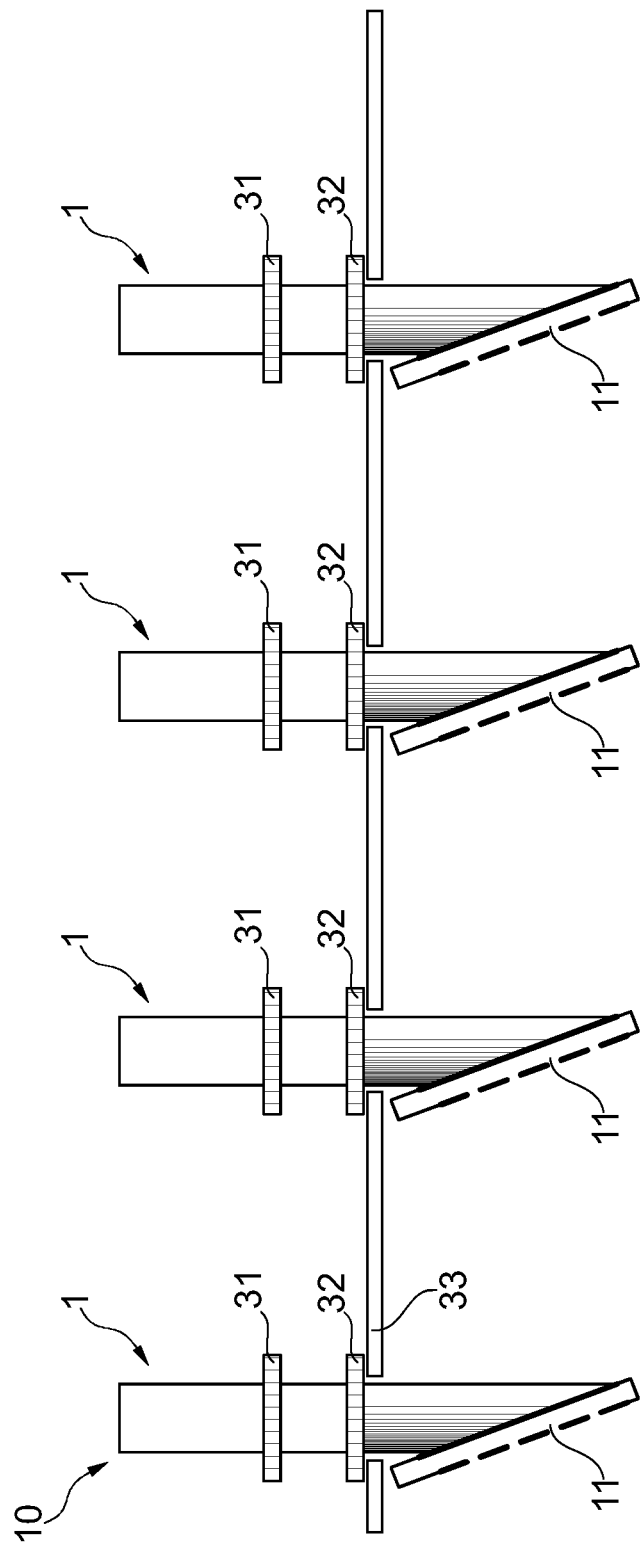
FIG. 2 shows a schematic drawing of an X-ray detector arrangement for X-ray phase contrast tomo-synthesis imaging according to the invention.

FIG. 2 shows schematically and exemplarily an X-ray detector arrangement 10 for X-ray phase contrast tomo-synthesis imaging according to the invention. Here, the relative arrangement of four line detectors 1 is shown. Any other number of line detectors 1 is also possible, e.g. 21 line detectors 1. The drawing is not for scale but indicates the small dimensions of each post-collimator 33 slit compared to the distance between two detector lines 11.

Several grating components (comprising a common source grating and each a phase grating 31 and an analyzer grating 32) configured to create a Moiré pattern in the X-ray beam 2 are shown in FIG. 2 as independently arranged in front of each line detector 1 when seen in the direction of the X-ray beam 2 (source grating is not shown). Not shown, but also possible is that one grating unit (source grating, phase grating 31 and analyzer grating 32) is arranged in front of and covers the entirety of all line detectors 1 at the same time when seen in the direction of the X-ray beam 2.

Figure 3:
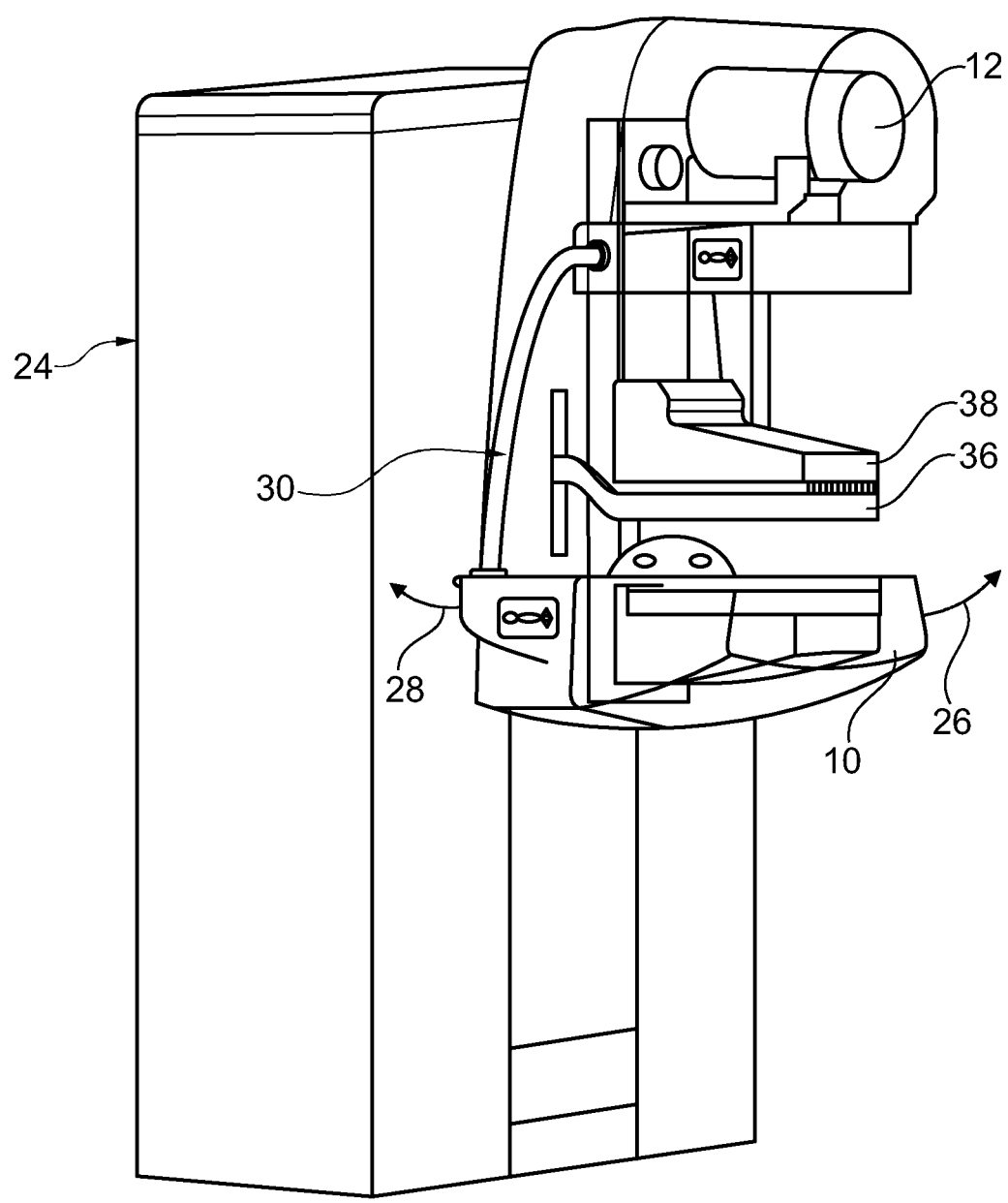
FIG. 3 shows a schematic drawing of an imaging system for X-ray phase contrast tomo-synthesis imaging of an object according to the present invention.

FIG. 3 shows a perspective view of a mammography system as an example for an imaging system 24 for X-ray phase contrast tomo-synthesis imaging of an object according to the present invention. The imaging system 24 comprises an X-ray source arrangement 12, a grating arrangement (not shown) and an X-ray detector arrangement 10 mounted to a gantry 30 or movement structure. The imaging system 24 further comprises an object support 36 or lower breast support paddle and an upper breast support paddle 38, which can be displaced in relation to each other in order to receive a breast to be examined as the object. For the acquisition, the breast stays in place and the gantry 30 during operation moves in relation to the breast. More specifically during operation the gantry 30 rotates, in directions 26 or 28, around an axis of rotation situated below the X-ray detector arrangement 10 when seen in the direction of an X-ray beam 2. It is also possible to implement a movement of the object, while the gantry 30 stays in place. The movement can be a rotational or a translational movement or a combination of both.

Figure 4:
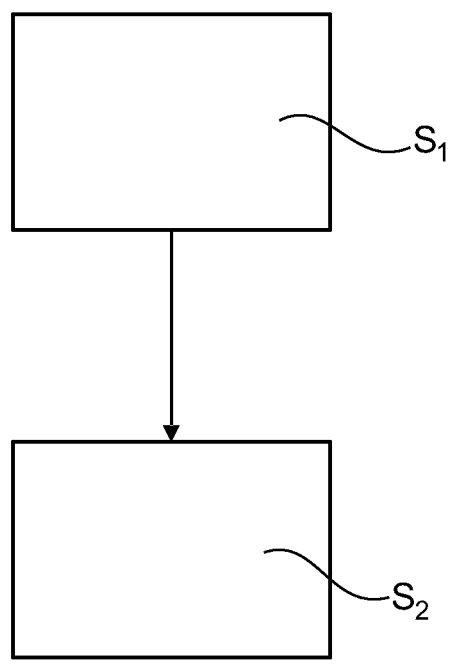
FIG. 4 shows a schematic overview of steps of an exemplary method for X-ray phase contrast tomo-synthesis imaging.

FIG. 4 shows a schematic overview of steps of an exemplary method for X-ray phase contrast tomo-synthesis imaging. The exemplary method comprises the following steps:

In a first step S1, providing an X-beam passing through an X-ray detector arrangement 10.

In a second step S2, detecting a Moiré pattern in at least a portion of the X-ray beam 2.

The X-ray detector arrangement 10 comprises several line detectors 1, wherein each line detector 1 is configured to detect the Moiré pattern in at least a portion of the X-ray beam 2. Each line detector 1 comprises several detector lines 11 and a width W of each line detector 1 equals one period or an integer multiple of the period of the Moiré pattern.

In an optional third step S3 (not shown), the exemplary method further comprises a using of the data detected by the detector lines 11 of each line detector 1 for generating images based on attenuation, phase-gradient and scatter information. The latter can be determined either by the Fourier method of phase-retrieval under the assumption that the spatial resolution in the scan direction is of the order of the width of a single line-detector followed by FBP reconstruction of the retrieved attenuation, phase-gradient and scatter information, or, if the above assumption is not valid, by a combined iterative reconstruction of the three images via phase detection or iterative reconstruction techniques.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it, which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An X-ray detector arrangement for X-ray phase contrast tomo-synthesis imaging, comprising:
    several line detectors, wherein each line detector is configured to detect a Moiré pattern, created by a grating arrangement, in at least a portion of an X-ray beam impacting the respective line detector, wherein each line detector comprises several independent detector lines, and wherein a width of each line detector equals one period or an integer multiple of the period of the Moiré pattern.

2. The X-ray detector arrangement according to claim 1, wherein each detector line is arranged along a direction perpendicular to an axis of symmetry of the X-ray beam.

3. The X-ray detector arrangement according to claim 1, wherein each detector line is inclined with an acute angle relative to an axis of symmetry of the X-ray beam.

4. An imaging system for X-ray phase contrast tomo-synthesis imaging of an object, comprising:
    a grating arrangement configured to create a Moiré pattern in an X-ray beam;
    an X-ray detector arrangement comprising several line detectors, wherein each line detector is configured to detect the Moiré pattern in at least a portion of the X-ray beam impacting the respective line detector, wherein each line detector comprises several independent detector lines, and wherein a width of each line detector equals one period or an integer multiple of the period of the Moiré pattern;
    an X-ray source arrangement; and
    a gantry, wherein the X-ray source arrangement, the grating arrangement and the X-ray detector arrangement are mounted to the gantry.

5. The imaging system according to claim 4, further comprising an object support configured to support the object, wherein the object support and the gantry are moveable.

6. The imaging system according to claim 4, wherein the imaging system is configured for rotating at least one of the gantry and the object support around an axis of rotation situated below the X-ray detector arrangement when seen in a direction of the X-ray beam.

7. The imaging system according to claim 5, wherein the imaging system is configured for translating at least one of the gantry and the object support in a direction perpendicular to an axis of symmetry of the X-ray beam.

8. A method for X-ray phase contrast tomo-synthesis imaging, comprising:
    providing an X-ray beam passing through an X-ray detector arrangement that comprises line detectors; and
    detecting a Moiré pattern, created by a grating arrangement, in at least a portion of an X-ray beam impacting the respective line detector, wherein each line detector comprises several detector lines, and wherein a width of each line detector equals one period or an integer multiple of the period of the Moiré pattern.

9. The X-ray detector arrangement according to claim 4, wherein the grating arrangement comprises several grating components configured to create a Moiré pattern in the X-ray beam such that one grating component is arranged in front of each line detector when seen in a direction of the X-ray beam.

10. The X-ray detector arrangement according to claim 4, wherein the grating arrangement comprises a grating unit configured to create a Moiré pattern in the X-ray beam such that the grating unit is arranged in front of and covers all line detectors at the same time when seen in a direction of the X-ray beam.

11. The X-ray detector arrangement according to claim 9, wherein each grating component comprises a phase grating and an analyzer grating.

12. The X-ray detector arrangement according to claim 10, wherein the grating unit comprises a phase grating and an analyzer grating.

13. A non-transitory computer-readable medium having one or more executable instructions stored thereon, which, when executed by a processor, cause the processor to perform a method for X-ray phase contrast tomo-synthesis imaging, the method comprising:
    providing an X-ray beam passing through an X-ray detector arrangement that comprises line detectors; and
    detecting a Moiré pattern, created by several grating components or a grating unit, in at least a portion of an X-ray beam impacting the respective line detector, wherein each line detector comprises several detector lines, and wherein a width of each line detector equals one period or an integer multiple of the period of the Moiré pattern.

* * * * *